United States Patent
Hwa et al.

(10) Patent No.: US 9,271,773 B2
(45) Date of Patent: Mar. 1, 2016

(54) BONE PLATE STRUCTURE

(75) Inventors: Su-Yang Hwa, Taipei (TW);
Shang-Chih Lin, Taipei (TW); Yu-Ling Chen, Taipei (TW); Yu-Ming Wang, Taipei (TW); Chu-An Luo, Taipei (TW)

(73) Assignees: NATIONAL TAIWAN UNIVERSITY OF SCIENCE AND TECHNOLOGY, Taipei (TW); TRI-SERVICE GENERAL HOSPITAL, Taipei (TW)

( * ) Notice: Subject to any disclaimer, the term of this patent is extended or adjusted under 35 U.S.C. 154(b) by 435 days.

(21) Appl. No.: 13/334,591

(22) Filed: Dec. 22, 2011

(65) Prior Publication Data
US 2012/0165878 A1 Jun. 28, 2012

(30) Foreign Application Priority Data
Dec. 24, 2010 (TW) .............................. 99224956 U

(51) Int. Cl.
| | |
|---|---|
| A61B 17/56 | (2006.01) |
| A61B 17/58 | (2006.01) |
| A61F 2/30 | (2006.01) |
| A61B 17/80 | (2006.01) |

(52) U.S. Cl.
CPC ........... *A61B 17/809* (2013.01); *A61B 17/8061* (2013.01); *A61B 17/8095* (2013.01)

(58) Field of Classification Search
USPC ...................... 606/70, 71, 280–283
See application file for complete search history.

(56) References Cited

U.S. PATENT DOCUMENTS

| | | | | |
|---|---|---|---|---|
| 7,052,499 | B2 * | 5/2006 | Steger et al. .................. | 606/291 |
| 2003/0199875 | A1 * | 10/2003 | Mingozzi et al. .............. | 606/69 |
| 2006/0241609 | A1 * | 10/2006 | Myerson et al. ................ | 606/69 |
| 2007/0043366 | A1 * | 2/2007 | Pfefferle et al. ................ | 606/69 |
| 2007/0123886 | A1 * | 5/2007 | Meyer et al. .................... | 606/70 |
| 2011/0319894 | A1 * | 12/2011 | Gupta ............................. | 606/70 |

* cited by examiner

*Primary Examiner* — Christopher Beccia
*Assistant Examiner* — Diana S Jones
(74) *Attorney, Agent, or Firm* — Thomas|Horstemeyer, LLP

(57) ABSTRACT

The present invention discloses an approximately π-shaped improved bone plate structure, fixed on a bone of an animal for maintaining the relative positions of different portions of the bone. One of the other features of the present invention is that bone plate structure comprises at least one contouring portion for allowing the surgeons to intra-operatively adjusting the shape in accordance with the shape of the bone. Furthermore, the present invention may fit the bone with multi-axis, decreasing stress concentration, preventing the opening portion from being unsuitably covered and preventing the wound deformation from being pressed.

3 Claims, 6 Drawing Sheets

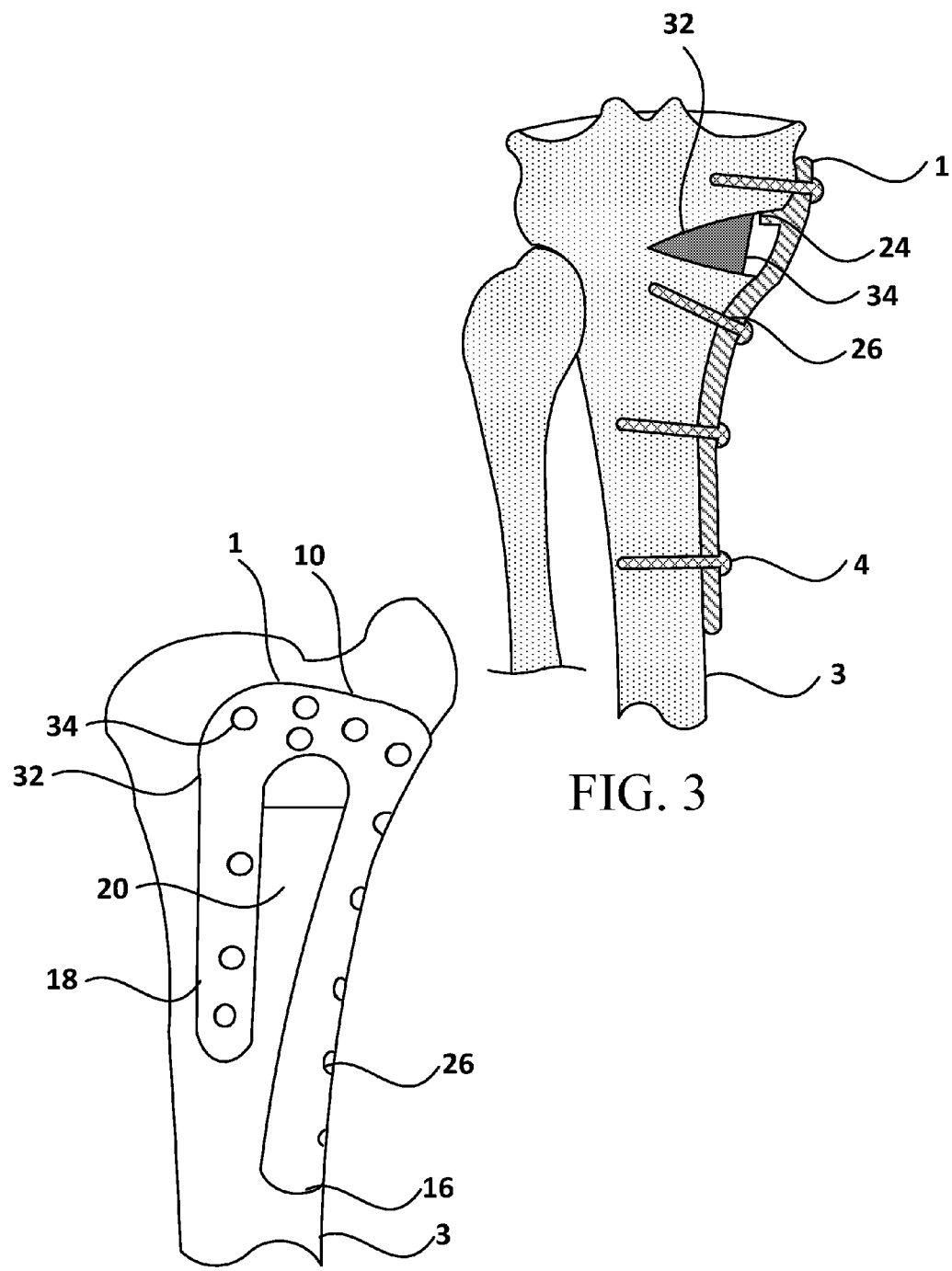

BONE PLATE STRUCTURE

CROSS-REFERENCE TO RELATED APPLICATION

Figure 1:
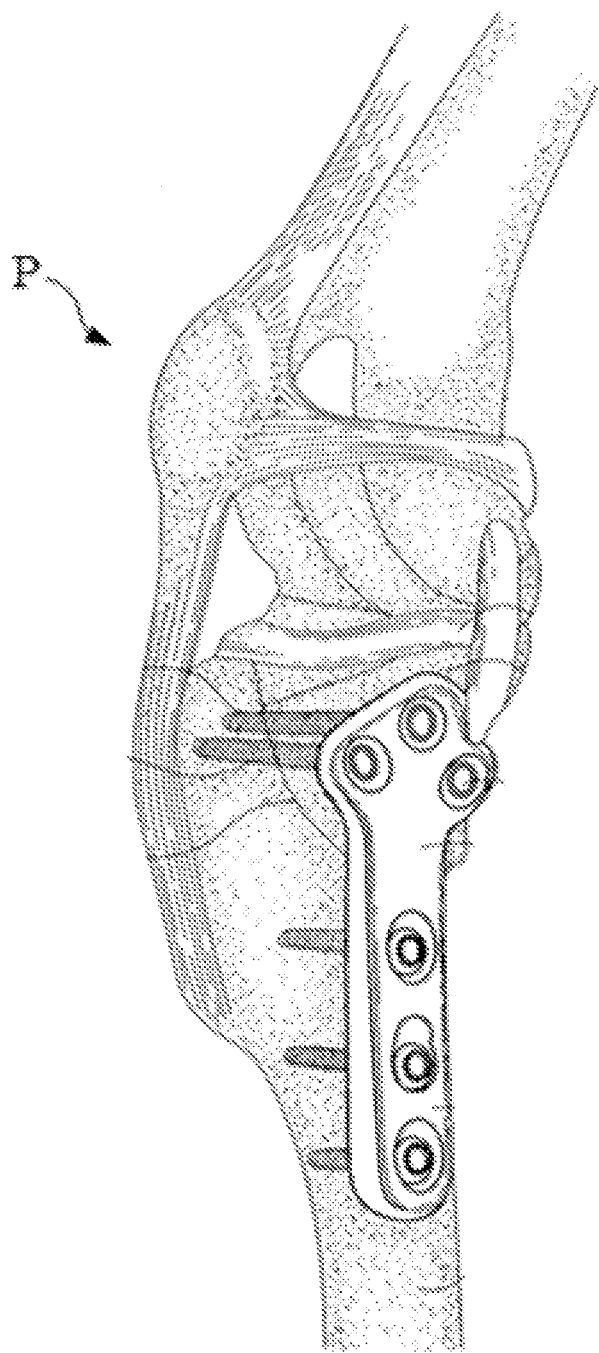

This application claims priority to Taiwan Application Serial Number 099224956, filed Dec. 24, 2010, which is incorporated herein by reference.

BACKGROUND OF THE INVENTION

1. Field of the invention

The present invention relates to an improved bone plate structure and more particularly, an approximately π-shaped improved bone plate structure.

2. Description of the prior art

Since the knee is one of the most important joints for bearing weight, the condition thereof affects the flexibility of action so as to relate to all activities required in daily life.

The symptom of degenerative arthritis of the knee generally comprises knee pain, knee weakness and lack of popliteal flexibility. Moreover, while the symptoms aggravate, pain occur on the proximal tibial articular surface of the knee, and may possibly causes the back pain, calf pain or ankle pain jointly. Meanwhile, the articular cartilage of medial knee gradually deteriorates to forms a varus knee due to the heavier loads at the medial condyle. Therefore, it is almost impossible for the sufferer to squat or to walk for a long time normally so as to seriously affect the quality of life of the sufferer.

However, with the development of medicine science, several treatments for curing the degenerative arthritis have been discovered recently. The treatments can be generally divided into two different aspects of medical treatment and surgical treatment. More specially, the surgical treatment may further comprises the treatment of total knee replacement and high tibial osteotomy.

Furthermore, the full artificial knee joint replacement treatment shall not be firstly considered since the artificial knee joint has plurality of disadvantages of expensive, relatively short service life, relatively high risk of infections and high difficulty and cost of treatment thereof unless the gonarthritis has already spread to the entire surface of the articular, or the gonarthritis is too serious for medicine treatment, or the knee pain of the sufferer cannot be retard consistently. Furthermore, after the full artificial knee joint replacement treatment, the sufferer shall no longer able to take the high strength sport such as running or mountaineering. Meanwhile, the allowable rotating angle of the knee is limited.

Therefore, instead of the full artificial knee joint replacement treatment, the treatment of high tibial osteotomy is preferred if the gonarthritis of the knee is only limited to only part of the proximal tibial articular surface.

A high tibial osteotomy looks to realign the knee to evenly share weight between both the inside and outside of the knee. This is achieved by cutting the bone and then taking a wedge of bone out at about two centimeters away from the tibial articular end, forming a filling portion thereon and adding a wedge of bone therein.

This high tibial osteotomy surgery has a long recovery period as the cut essentially fractures the main weight bearing bone of the lower leg. Even after surgically fixing the bone in its new position, it is unable to take any weight for a significant period of time. This has a major implication for work, lifestyle and everyday activities.

Accordingly, a bone plate structure is required to reinforce the bone after the surgery so as to share the weight of the sufferer in order to avoid the fracture of the tibial. Traditionally, the bone plates are T shaped, I shaped or L shaped which is only capable of covering a small and very limited portion of the proximal tibial articular surface. Please refer to the FIG. 1, FIG. 1 depicted a schematic figure of an I-shaped bone plate of a prior art. In the Taiwan patent publication No. 200800094, the reference discloses an I-shaped bone plate having a small head portion which is utilized to be fixed on the proximal tibial articular surface. Since the surface area of head portion of the bone plate becomes very limited, the bone plate is relatively difficult to be fixed on the surface previously described and the bone plate may has loosing and shaking problem. Moreover, the bone plate structure may deform because of the stress concentration, damaging the bone plate inside of the body of the sufferer and hurting the sufferer. Furthermore, the traditional bone plate design covers the filling portion, retarding the user to observe or to process any treatment to the wound of the said opening filling portion via the tradition bone plate.

Therefore, a need exists to develop a bone plate which is capable of fitting the bone with multi-axis, decreasing stress concentration, preventing the opening filling portion from being unsuitably covered and preventing the wound deformation from being pressed by minimum cost.

SUMMARY OF THE INVENTION

One aspect of the present invention is to provide an improved bone plate structure, fixed on a bone of an animal for maintaining the relative positions of different portions of the bone. The improved bone plate structure is characteristic in that it is approximately π shaped.

Another aspect of the present invention is to provide an improved bone plate structure, fixed on a bone of an animal for maintaining the relative positions of different portions of the bone, which comprising a plate body, a first extension portion and a second extension portion. The first extension portion has a first length and extending outwardly from a lateral surface of the plate body along the normal vector of the lateral surface substantially. The second extension portion has a second length and extending outwardly from the lateral surface of the plate body along the normal vector of the lateral surface substantially and converging with the first extension portion.

In actual practice, the displacement among the first extension portion and the second extension portion decreases as the extending length of the first extension portion and the second extension portion increases correspondingly while the first extending length of the first extension portion is not longer than the second length, wherein the first length of the first extending portion is longer than the second length of the second extending portion.

Furthermore, the present invention further comprises a contouring portion, for intra-operatively adjusting the force of contouring the improved bone plate structure, which the contouring portion may comprises a groove or a plurality of hemisphere-shaped hollows.

Meanwhile, the supporting structure may be placed against a lateral of an opening portion formed on the bone for reinforcing the opening portion, wherein the supporting structure may be disposed on the first extension portion or the second extension portion. Furthermore, the present invention may further comprises a plurality of through holes, each of the through holes being capable of allowing a bone nail to penetrate therethrough so as to fix the improved bone plate on the bone.

The objective of the present invention will no doubt become obvious to those of ordinary skill in the art after reading the following detailed description of the preferred embodiment, which is illustrated in following figures and drawings.

BRIEF DESCRIPTION OF THE APPENDED DRAWINGS

FIG. 1 depicted a schematic figure of an I-shaped bone plate of a prior art.

Figure 2A:
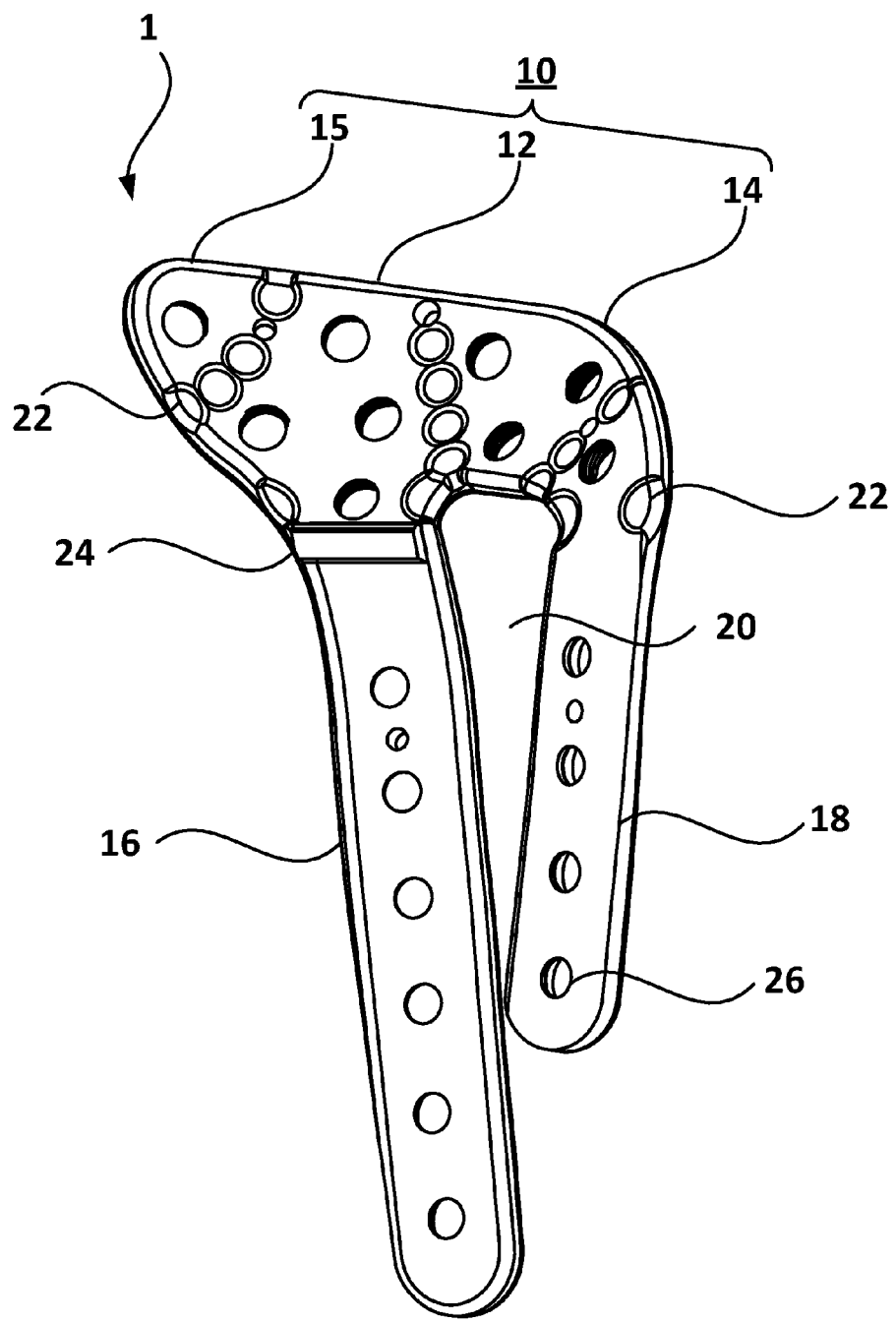

FIG. 2A depicted a schematic figure of the improved bone plate structure of an embodiment of the present invention from a viewpoint.

Figure 2B:
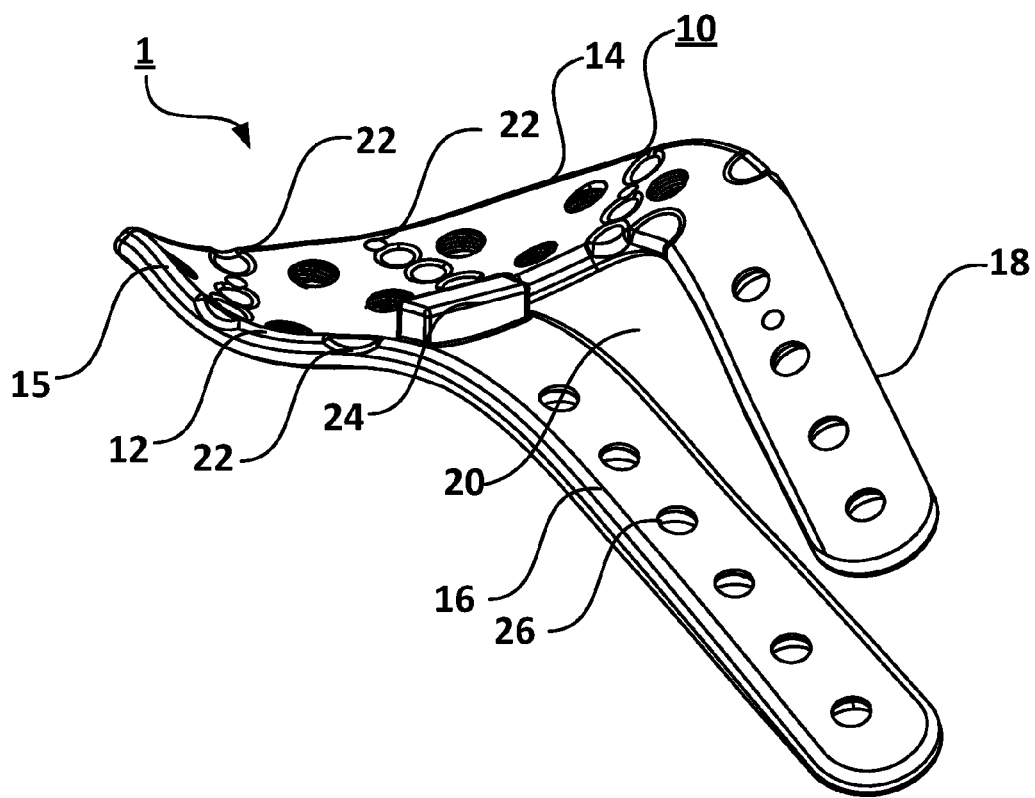

FIG. 2B depicted a schematic figure of the improved bone plate structure of an embodiment of the present invention from another viewpoint.

Figure 2C:
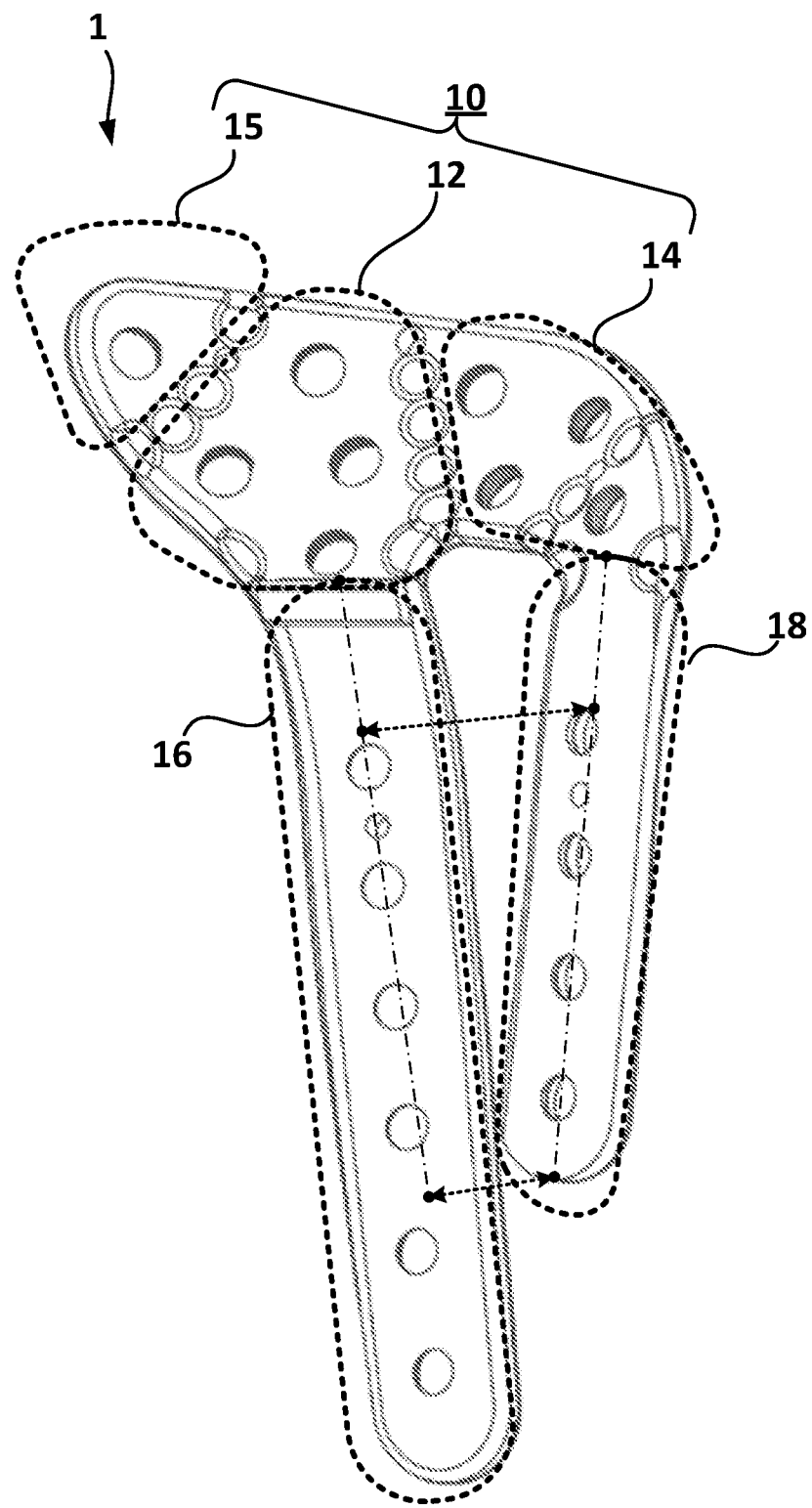

FIG. 2C depicted another schematic figure of the improved bone plate structure of an embodiment of the present invention from the same viewpoint as FIG. 2A.

FIG. 3 depicted a section plane view of the improved bone plate structure of an embodiment of the present invention while in use.

FIG. 4 depicted a schematic figure of the improved bone plate structure on application of an embodiment of the present invention.

Figure 5:
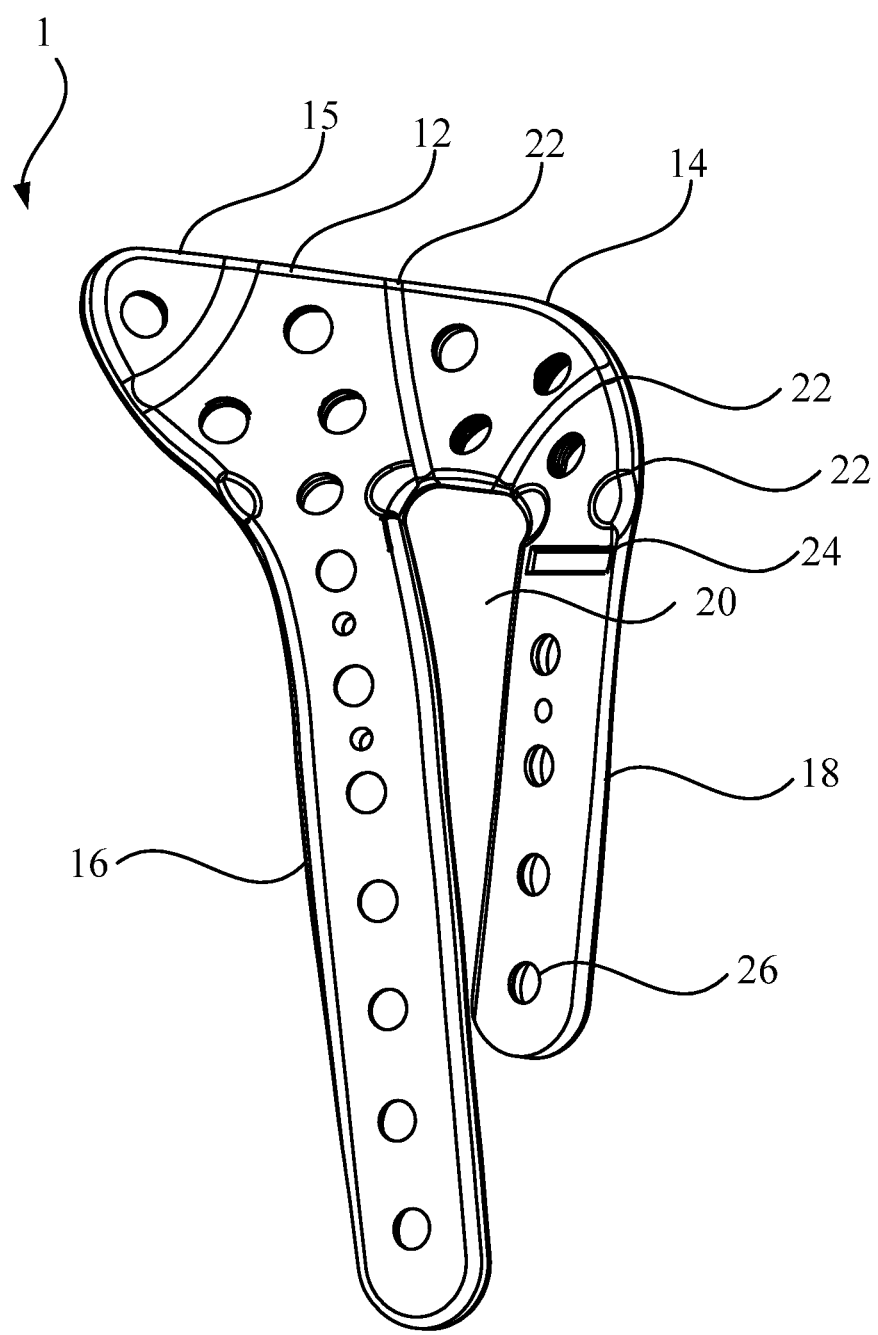

FIG. 5 is a schematic figure of the improved bone plate structure of another embodiment of the present invention.

DETAILED DESCRIPTION OF THE INVENTION

First of all, it should be noticed that the present application is based on, and claims priority from, Taiwan Application Serial Number 099224956, filed Dec. 24, 2010. The disclosure of which is hereby incorporated by reference herein in its entirety.

Please refer to the FIG. 2A to FIG. 2C, FIG. 2A and FIG. 2C depicted two different schematic figures of the improved bone plate structure of an embodiment of the present invention from the same viewpoint. FIG. 2B depicted a schematic figure of the improved bone plate structure of an embodiment of the present invention from another viewpoint. It should be noticed that the FIG. 2A to FIG. 2C are undistorted model of the present invention, therefore, the dimensions and the configuration shown by the figure should be able to be treated as the concrete features of the present invention.

Please refer to the FIG. 2A to FIG. 2C, in the present embodiment, the improved bone plate structure 1 of the present invention generally comprises a plate body 10, a first extension portion 16, a second extension portion 18, a space portion 20, a contouring portion 22 and a supporting structure 24, wherein the plate body 10 is generally formed by a first portion 12, a second portion 14 and a third portion 15. Each of the said first portion 12, a second portion 14 and a third portion 15 may be covered and fixed to the different surfaces having different axial of the tibial respectively so as to overcome the strain concentration problem causes by the one single surface design of the traditional bone plate as previously described.

It worth a mention that the improved bone plate structure 1 of the present invention can be, but not limited to, formed by an one-piece formed process, which mean all of the components are basically formed by a single piece of material by machining thereto. However, the improved bone plate structure can also be formed by assembling plurality of components together. Meanwhile, the improved bone plate structure 1 can be, but not limited to, formed by stainless steel, titanium, titanium alloy or any other possible non-metal material that not be listed. In the embodiment of the present invention, the improved bone plate structure 1 of the present invention is configured on the proximal tibial articular surface. Furthermore, apart from tibia, the improved bone plate structure 1 of the present invention can also be utilized on any other bone or articular surface in accordance with the needs or requirements of the user. It worth a mention that, the improved bone plate structure 1 can be utilized on the other animal apart from hominoid, such as canine, feline, bovine, equine or the others.

Please refer to the FIG. 2A and 2B again, it is clearly shown that one of the main features of the present invention is that the improved bone plate structure 1 having an approximately π shape structure. More specially, the first extension portion 16 and the second extension portion 18 has a total length of a first length and a second length respectively. The first extension portion 16 and the second extension portion 18 is formed on a lateral surface of the plate body 10 and extending outwardly therefrom substantially along the normal vector of the lateral surface so as to converge mutually with each other, wherein, in the present embodiment, the first length of the first extending portion 16 is longer than the second length of the second extending portion 18. The term substantially previously described means that the extending direction thereof may allow a degree error smaller than 20 degrees. Furthermore, the term "converge mutually" previously described actually means that the distance among the first extension portion 16 and the second extension portion 18 decreases as the extending length of the first extension portion and the second extension portion increases correspondingly while the first extending length of the first extension portion 16 is not longer than the second length.

Furthermore, by the FIG. 2A and FIG. 3, it is clearly shown that the plate body 10, the first extension portion 16 and the second extension portion 18 surrounds to form a space portion 20. By the design of space portion 20, the surgeons may observe, diagnose the opening portion 32 formed on the surface of the bone via the space portion 20 previously described. Accordingly, the repeatedly installation and removal of the improved bone plate structure 1 can be omitted so as to minimize the damage of the bone surface. In the embodiment of the present invention, the first portion 12, the second portion 14 and the third portion 15 are fixed on proximal tibial articular surface, positioned above the opening portion 32, wherein the first extension portion 16 and the second extension portion 18 are fixed on the area below the proximal tibial articular surface or the flanking of the tibia 3.

In the present embodiment, the improved bone plate structure 1 further comprises at least one contouring portion 22. Each of the contouring portions 22 is disposed or formed on a surface of the improved bone plate structure 1, for adjusting the intensity of the improved bone plate structure 1 and allowing the surgeon to intra-operatively adjusts the force required to contour or deform the shape of the improved bone plate structure 1. Accordingly, the medical surgeons is capable of contouring and adjusting the shape of the improved bone plate structure 1 of the present invention so as to fit the animal bone surface via a corresponding hand tool of the improved bone plate structure 1, avoiding the loosing and shaking problem of the bone plate. The contouring portion 22 may be formed on the random or predetermined position on the surface of the improved bone plate structure 1 in accordance with the needs of the user, therefore, the description thereof shall be omitted herein.

Moreover, for improving the mechanical properties of the improved bone plate structure 1 of the present invention, the contouring portion 22 is formed by a press molding process by stamping or pressing a pressing head having a predetermined shape onto the surface of the improved bone plate structure 1 so as to form a hollow portion with a pre-determined shape thereon. In the embodiment of the present invention, the pre-determined shape of the contouring portion 22 previously described may comprises a plurality of hemisphere-shaped hollows arranged in a linear form or a relatively long groove as shown in FIG. 5. Furthermore, it worth a mention that the contouring portion 22 of the present invention can be omitted due to the improved bone plate structure 1 may be custom designed for the sufferer which no contour or adjustment is required.

Please refer to the FIG. 4, FIG. 4 depicted a schematic figure of the improved bone plate structure on application of an embodiment of the present invention. The figure is clearly shown that the first portion 12, the second portion 14 and the third portion 15 are fixed to different surfaces of the articular having different axis via at least one bone nail 4 respectively for increasing the covering and contacting area thereof to provide a stable support to the bone as decreasing the loosening and shaking of the bone plate. It worth a mention that, the first portion 12, the second portion 14 and the third portion 15 is not limited to be fixed on different surfaces of the articular, which means the first portion 12, the second portion 14 and the third portion 15 can be fixed on a single surface.

Please refer to the FIG. 3, FIG. 3 depicted a section plane view of the improved bone plate structure of an embodiment of the present invention while in use. In the embodiment of the present invention, the improved bone plate structure 1 is applied in the high tibial osteotomy for fixing the tibia 3. In the high tibial osteotomy, the medical surgeon will cut a bone, which is approximately two centimeters away from the articular surface of the tibia 3, to form an opening portion 32, and fill a filling element 34 in the opening portion 32 for forcing the tibia 3 to turn out, so as to adjust the mechanics axis of the tibia 3 to the normal position, then the improved bone plate structure 1 is fixed on the tibia 3 in the upper portion and the bottom portion of the opening portion 32, for distributing the joint stress and helping the healing of the bone.

Please refer to the FIG. 2A, it is clearly shown that the supporting structure 24 is placed against a lateral of an opening portion formed on the bone for reinforcing the opening portion. More specifically, the supporting structure 24 disposed on the first extension portion 16, for reinforcing and holding the hollow of the opening portion 32 and fixing the position of the opening portion 32 so as to prevent the deformation of the opening portion 32 due to the force accepted by the tibia while the animal takes an activity with high intensity. Please refer to the FIG. 3, as shown in FIG. 3, the fitting condition of the opening portion 32 of the improved bone plate structure 1 of the present invention is expressed clearly. Furthermore, please refer to the FIG. 5 again, it is clearly shown that the supporting structure 24 can also be formed or be disposed on the surface of the second extension portion 18.

Moreover, the improved bone plate structure 1 may further comprises a plurality of through holes 26. The holes 26 are formed on the plate body 10, the first extension portion 16, the second extension portion 18 as shown in the figure. However, in actual practice, the holes 26 can be formed in another pattern in accordance with the needs of the user. The holes 26 is capable of allowing the bone nail 4 to penetrate the improved bone plate structure 1 so as to fix the improved bone plate 1 on the animal bone thereby. In the embodiment of the present invention, each hole 26 has a thread respectively, but the thread is not necessary.

In summary, the present invention discloses an approximately π-shaped improved bone plate structure, fixed on a bone of an animal for maintaining the relative positions of different portions of the bone. One of the other features of the present invention is that the bone plate structure comprises at least one contouring portion for allowing the surgeons to intra-operatively adjust the shape in accordance with the shape of the bone. Furthermore, the present invention may fit the bone with multi-axis, decreasing stress concentration, preventing the opening portion from being unsuitably covered and preventing the wound deformation from being pressed.

Although the present invention has been illustrated and described with reference to the preferred embodiment thereof, it should be understood that it is in no way limited to the details of such embodiment but is capable of numerous modifications within the scope of the appended claims.

What is claimed is:

1. An improved bone plate structure, fixed on a bone of an animal for maintaining the relative positions of different portions of the bone, comprising:
   a plate body, having an inner surface, the inner surface being adapted to contact with the bone of the animal, the plate body having a first portion and a second portion;
   a first extension portion, having a first length, extending outwardly from a lateral surface of the first portion of the plate body along a normal vector of the lateral surface of the first portion substantially, wherein the normal vector of the lateral surface of the first portion is an axis for the first extension portion;
   a second extension portion, having a second length, extending outwardly from a lateral surface of the second portion of the plate body along a normal vector of the lateral surface of the second portion substantially and converging with the first extension portion, wherein the normal vector of the lateral surface of the second portion is an axis for the second extension portion;
   a supporting structure, disposed on one of the first extension part and the second extension part for placing against a lateral of an opening portion formed on the bone for reinforcing the opening portion; and
   a contouring portion, configured on the inner surface, for intra-operatively adjusting the force of contouring the plate body, the contouring portion having a groove formed on the inner surface between the first portion and the second portion of the plate body while the groove being formed of a plurality of interconnected hemisphere-shaped hollows.

2. The improved bone plate structure of claim 1, wherein a displacement among the first extension portion and the second extension portion decreases as the extending length of the first extension portion and the second extension portion increases correspondingly while the first extending length of the first extension portion is not longer than the second length.

3. The improved bone plate bone plate structure of claim 1, further comprising a plurality of through holes, each of the through holes being capable of allowing a bone nail to penetrate therethrough so as to fix the improved bone plate on the bone.

* * * * *